United States Patent
Beaver

[19]

[11] Patent Number: 5,827,235
[45] Date of Patent: Oct. 27, 1998

[54] METHOD AND APPARATUS USED TO APPLY TOPICAL MEDICATION

[76] Inventor: George M. Beaver, 4190 Ridgewood Ave., Port Orange, Fla. 32127

[21] Appl. No.: 771,521

[22] Filed: Dec. 23, 1996

[51] Int. Cl.$^6$ .................................................. A61M 5/315
[52] U.S. Cl. ..................... 604/236; 604/181; 604/231; 604/218; 222/386; 222/450
[58] Field of Search ........................................ 604/181, 187, 604/190, 191, 218, 213, 256, 257, 247, 246, 184, 236, 215, 231; 222/386, 387, 450

[56] References Cited

U.S. PATENT DOCUMENTS

| | | | |
|---|---|---|---|
| 3,437,242 | 4/1969 | Paitias | 222/135 |
| 3,917,124 | 11/1975 | Kifer | 222/386 |
| 4,403,986 | 9/1983 | Dettbarn et al. | |
| 4,793,521 | 12/1988 | Steiner | 222/156 |
| 5,026,343 | 6/1991 | Holzer . | |
| 5,064,413 | 11/1991 | McKinnon et al. . | |
| 5,074,843 | 12/1991 | Dalto et al. . | |
| 5,256,142 | 10/1993 | Colavecchio . | |
| 5,501,666 | 3/1996 | Spielberg . | |

Primary Examiner—Wynn Wood Coggins
Assistant Examiner—Cris L. Rodriguez
Attorney, Agent, or Firm—Paul S. Rooy

[57] ABSTRACT

A method and apparatus for dispensing topical medication. The apparatus consists of a dispenser comprising a piston assembly slidably engaged with a housing, and a nozzle frictionally attached to the housing. The housing comprises an upper reservoir, lower reservoir and nozzle reservoir. The piston assembly comprises a piston attached to a rod, the rod reciprocating within a housing rod aperture, and the piston reciprocating within a housing bore. The upper reservoir is defined by a housing top, the housing bore, and the piston. The lower reservoir is defined by the piston, housing bore, and a lower reservoir floor. The upper reservoir communicates with the exterior of the housing by means of a normally closed upper reservoir valve, and with the lower reservoir by means of a normally open piston valve. The nozzle reservoir communicates with the lower reservoir through a normally closed lower reservoir valve, and with the exterior of the housing through a stem bore in a housing stem, and through a nozzle outlet. The method comprises the steps of locating pores in an area to which topical medication is to be administered, massaging skin around each pore until each pore is open, and applying medication to each pore using the dispenser.

9 Claims, 3 Drawing Sheets

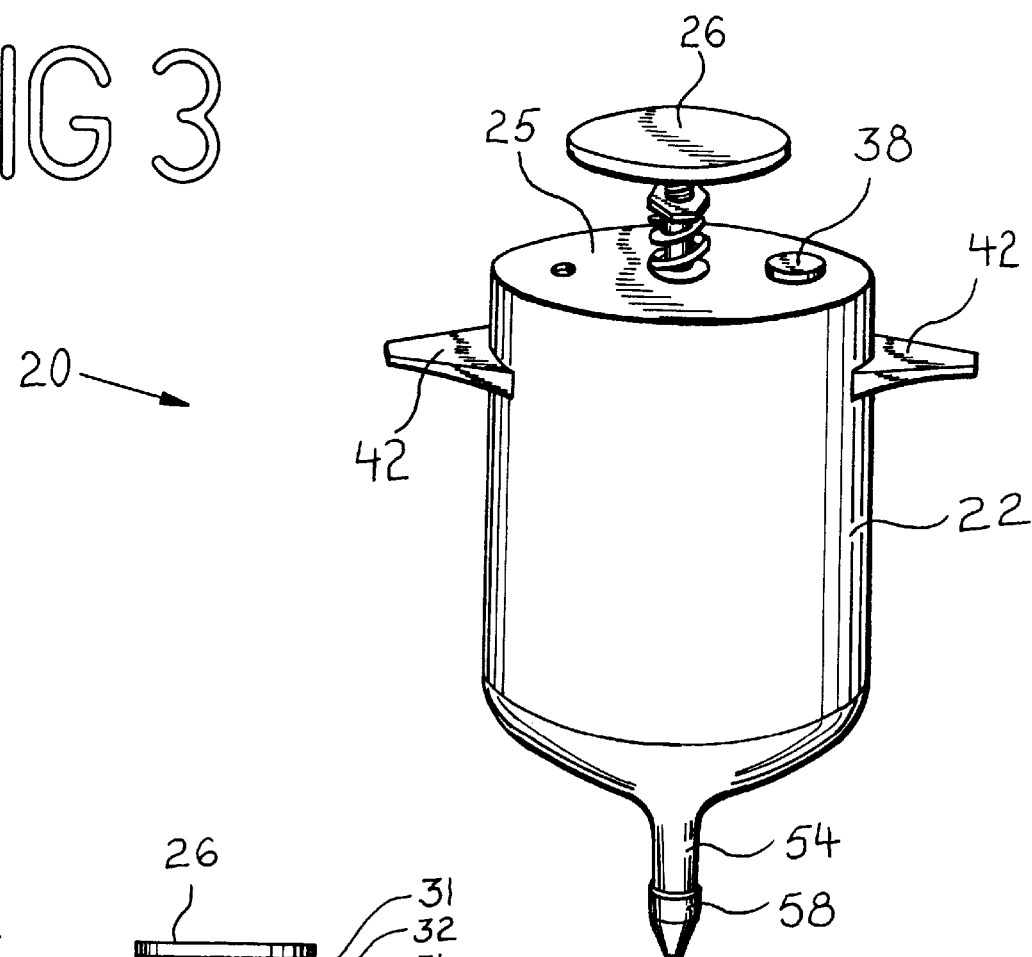
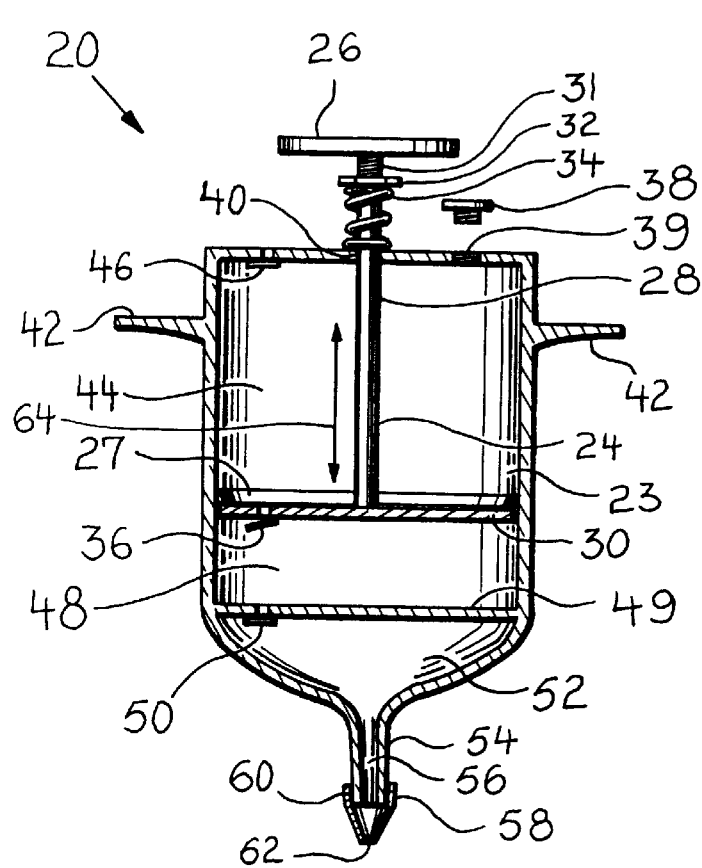

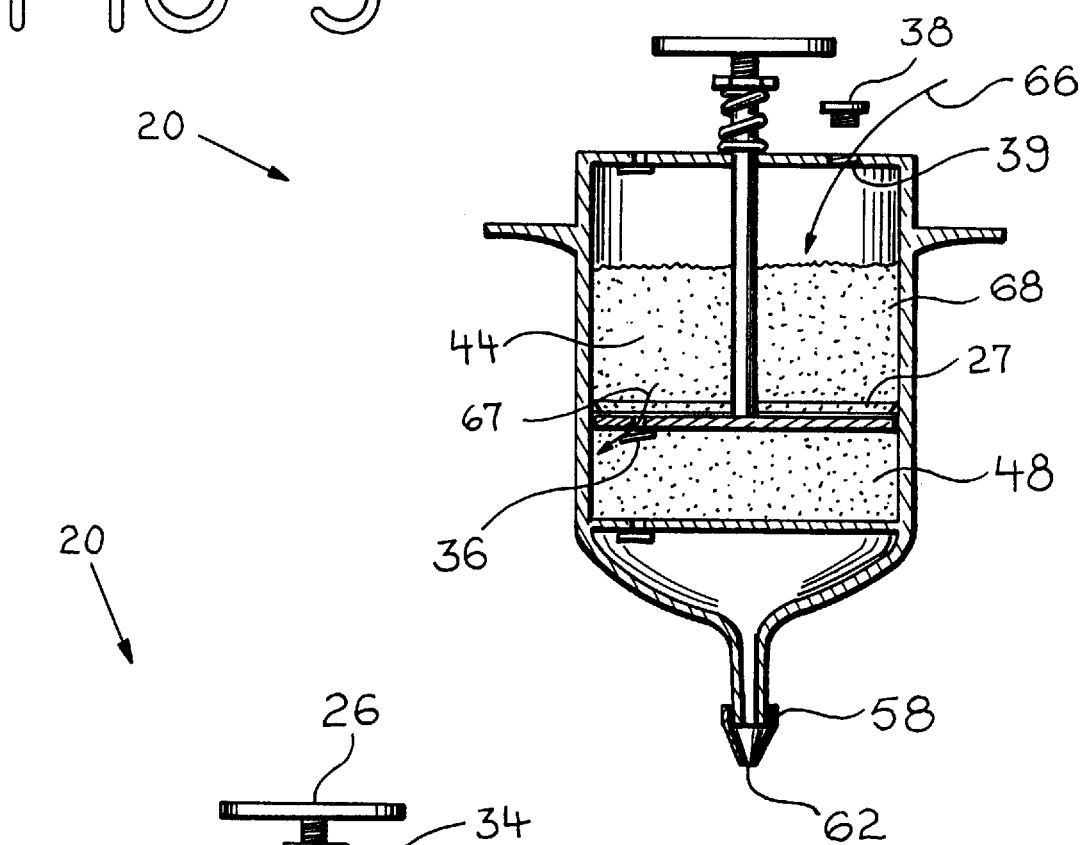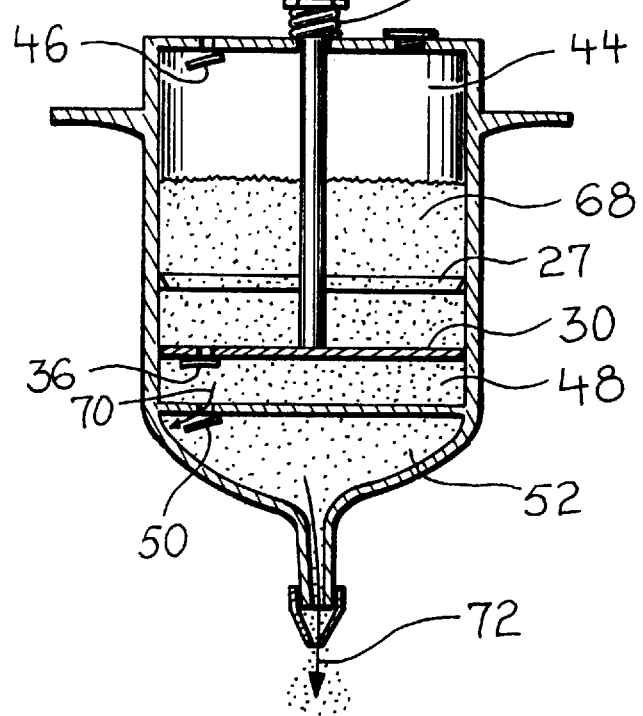

METHOD AND APPARATUS USED TO APPLY TOPICAL MEDICATION

BACKGROUND OF THE INVENTION

1. Field of the Invention

This invention relates to the administration of medication, and in particular to a method and apparatus used to apply topical medication.

2. Backbround of the Invention

Topical medication is defined as that medication which pertains to, or is applied to, an isolated part of the body. Examples include hair growth drugs which are generally applied to the scalp, heating creams for muscle pain, and anti-fungal foot powder. Topical medication is typically in salve or liquid form, and must be rubbed onto the part of the body which it is intended to help. Once applied, the topical medication is absorbed into the skin in order to accomplish its task.

One avenue which topical medication uses to gain access through the skin are the pores of the human body. Pores are the external openings of skin sweat glands. By way of example, the human skull contains thousands of pores. A hair growth solution applied to the scalp is absorbed through the scalp skin, and filters through to the arteries in part via the pores. Arteries and veins are both disposed in close proximity to the sweat glands.

FIG. 1 is a side cross-sectional view of typical human skin 2. Skin 2 is comprised of an outer layer, epidermis 4, and an inner layer, dermis 6. Skin 2 is attached to the rest of the body by means of connective fibrous tissue 8. Sweat glands 10 and hairs 18 are anchored in dermis 6, and access the outside of the skin through epidermis 4. Sweat glands 10 terminate in pores 12.

Skin arteries and veins are disposed in close proximity to the sweat glands. As may be observed in FIG. 1, there are a number of arterioles 14 and venules 16 close to sweat gland 10. Thus medication which enters a sweat gland 10 through a pore 12 may readily further migrate to an arteriole 14.

FIG. 2 is a top view of a typical pore 12. Each pore 12 is shaped like a slit, and contains a stiff thistle 19. Thistle 19 extends approximately to the level of the surface of skin 2 within which pore 12 resides.

As was previously mentioned, current application techniques for applying topical medication include the steps of placing the medication onto the skin in the appropriate place, and then rubbing it in until it is absorbed into the skin. One problem associated with this approach is that the topical medication will be spread equally on the epidermis having no pores, as on the pores themselves. The fastest and most efficient route to the arteries for some topical medication is through the pores and sweat glands. In these cases, the most effective application point is directly over the pores themselves. An example of one such drug is hair growth medication. If this type of medication is spread indiscriminately over epidermis without pores and epidermis with pores, the medication will not be as effective as if it were applied only to the pores themselves. If merely spread over the skin, this type of medication would be to some extent wasted, and its effectiveness would suffer.

Another method of application of topical drugs is via hypodermic syringe. Drawbacks associated with this method of medication delivery are the fact that the skin is (sometimes painfully) punctured, and the attendant health risks.

SUMMARY OF THE INVENTION

Accordingly, it is an object of the present invention to provide a method and apparatus used to apply topical medication which is more effective than conventional methods. Method features allowing this object to be accomplished include the steps of locating pores, massaging the skin in the vicinity of the pores until the pores are open, and applying medication over the pores themselves. Advantages associated with the accomplishment of this object include more effective medication administration, and less waste of medication.

It is another object of the present invention to provide a method and apparatus used to apply topical medication which does not involve puncturing the skin. Apparatus design features allowing this object to be accomplished include a dispenser with a piston and nozzle. Benefits associated with the accomplishment of this object include reduced patient discomfort, and decreased health risk.

It is yet another object of this invention to provide a method and apparatus used to apply topical medication which is inexpensive. Design features allowing this object to be achieved include the use of components made of readily available materials. Benefits associated with reaching this objective include reduced cost, and hence increased availability.

BRIEF DESCRIPTION OF THE DRAWINGS

The invention, together with the other objects, features, aspects and advantages thereof will be more clearly understood from the following in conjunction with the accompanying drawings.

Three sheets of drawings are provided. Sheet one contains FIGS. 1 and 2. Sheet two contains FIGS. 3 and 4. Sheet three contains FIGS. 5 and 6.

FIG. 3 is a side isometric view of a dispenser.

FIG. 4 is a side cross-sectional view of a dispenser.

FIG. 5 is a side cross-sectional view of a dispenser being filled.

FIG. 6 is a side cross-sectional view of a dispenser after a piston down stroke.

DETAILED DESCRIPTION OF THE PREFERRED EMBODIMENT

Figure 1:
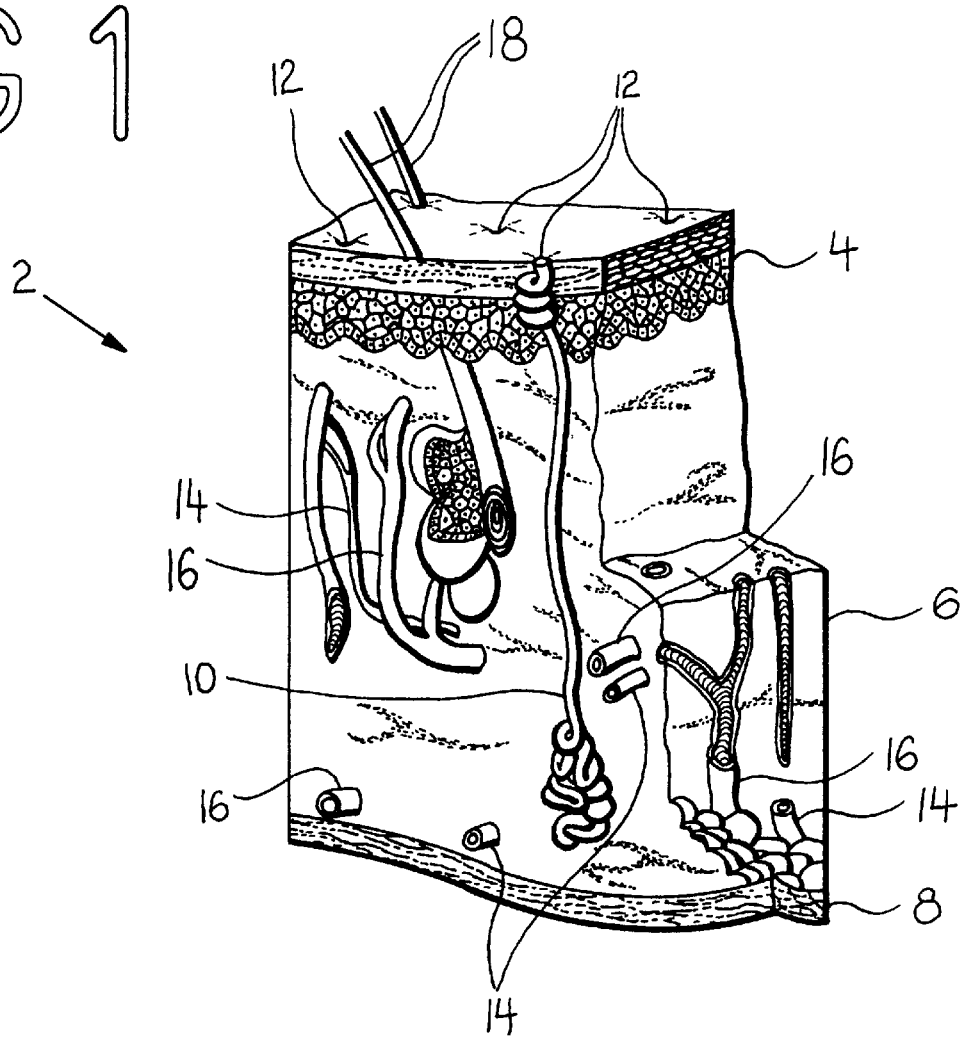
FIG. 1 is a front cross-sectional view of typical human skin.
Figure 2:
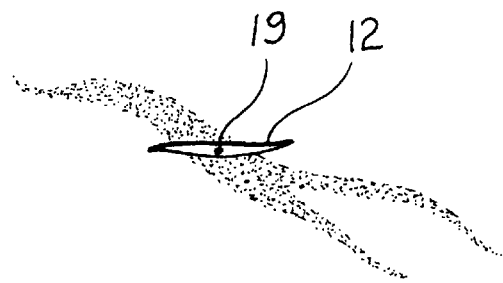
FIG. 2 is a top view of a pore.

The instant invention method comprises the steps of finding pores, massaging the pores until they are open, and then administering medication directly onto the pores. A dispenser is used to administer topical medication directly onto the appropriate pores. FIG. 3 is a side isometric view of dispenser 20. FIG. 4 is a side cross-sectional view of dispenser 20.

Dispenser 20 comprises a piston assembly 24 slidably engaged with a housing 22, and a nozzle 58 frictionally mounted onto housing 22. Housing 22 comprises housing top 25, housing bore 23, upper reservoir 44, lower reservoir 48 and nozzle reservoir 52. Upper reservoir 44 communicates with lower reservoir 48 through piston valve 36. Lower reservoir 48 communicates with nozzle reservoir 52 through lower reservoir valve 50. Piston valve 36 is a normally open valve which closes when the pressure in lower reservoir 48 exceeds the pressure in upper reservoir 44 by a pre-set amount equivalent to that pressure differential necessary to overcome any gravity caused pressure difference that exists by virtue of medication within lower reservoir 48 supporting the weight of medication within upper reservoir 44. Lower reservoir valve 50 is a normally closed valve which opens when the pressure in lower reservoir 48 exceeds a threshold pressure.

Note that upper reservoir 44 is defined by housing bore 23, housing top 25 and piston 30. Lower reservoir 48 is defined by housing bore 23, piston 30 and lower reservoir floor 49. The sizes of upper reservoir 44 and lower reservoir 48 change as piston 30 reciprocates within housing bore 23 as indicated by arrow 64.

Upper reservoir 44 communicates with the exterior of housing 22 through upper reservoir valve 46 and cap aperture 39. Cap 38 fits into cap aperture 39. Cap aperture 39 is used to fill dispenser 20 with topical medication. Upper reservoir valve 46 is a normally closed valve which opens when the pressure outside housing 22 exceeds the pressure within upper reservoir 44.

Housing 22 further comprises rod aperture 40 communicating with upper reservoir 44, and stem 54 having stem bore 56. Nozzle reservoir 52 communicates with the exterior of dispenser 20 through stem bore 56. Dispenser 20 further comprises a nozzle 58 having nozzle stem bore 60 and nozzle outlet 62. Nozzle stem bore 60 is sized to frictionally admit stem 54. Stem bore 56 communicates with the exterior of dispenser 20 through nozzle outlet 62. Nozzles 58 are available with different nozzle outlet 62 sizes, and may be easily changed so as to provide the proper nozzle outlet 62 size.

In addition, housing 22 comprises finger rests 42 rigidly attached to its outer surface. Finger rests 42 serve to provide a grip against which to push thumb rest 26, when dispenser 20 is being used to dispense medication.

Piston assembly 24 comprises thumb rest 26 attached to one extreme of rod 28, and piston 30 attached to an opposite extreme of rod 28. Rod 28 is sized to slidably fit through rod aperture 40. Piston 30 is sized to reciprocate within housing bore 23 as indicated by arrow 64. The extreme of rod 28 to which thumb rest 26 is attached is threaded with rod thread 31. Nut 32 is engaged with rod thread 31. The position of nut 32 along rod 28 determines the stroke length of piston 30, and thus the dosage of medication administered per stroke of piston 30. Spring 34 is disposed around rod 28, and is trapped between nut 32 and housing top 25. Spring 34 urges thumb rest 26 away from housing top 25, and piston 30 into contact with stop 27. Stop 27 is disposed on housing bore 23, and defines the upper limit of the piston 30 stroke.

In operation, dispenser 20 is first filled, and then multiple sequential dosages may be administered by depressing thumb rest 26. FIG. 5 is a side cross-sectional view of a dispenser being filled, and FIG. 6 is a side cross-sectional view of a dispenser after piston 30 has been depressed.

As may be observed in FIG. 5, dispenser 20 is filled with medication 68 through cap aperture 39 as indicated by arrow 66. Because piston valve 36 is normally open, medication 68 fills both upper reservoir 44 and lower reservoir 48 as indicated by arrow 67. After filling, cap 38 is repositioned into cap aperture 39, and nut 32 adjusted for the proper dosage. Nozzle 58 may be replaced so as to vary the size of nozzle outlet 62.

Nozzle outlet 62 is then positioned as desired over an appropriate pore 12, and thumb rest 26 is depressed until spring 34 is fully collapsed, thus terminating the piston 30 downstroke. As piston 30 descends, atmospheric pressure external to housing 22 forces upper reservoir valve 46 open, thus relieving the vacuum that would otherwise exist within upper reservoir 44 impeding the piston 30 downstroke. Simultaneously, the downward travel of piston 30 creates pressure within lower reservoir 48 that exceeds pressure within upper reservoir 44, and when pressure within lower reservoir 48 exceeds pressure within upper reservoir 44 by a pre-set amount, piston valve 36 closes. With piston valve 36 closed, the only avenue of escape for medication 68 is through lower reservoir valve 50 as indicated by arrow 70.

The downstroke of piston 50 also causes greater pressure within lower reservoir 48 than within nozzle reservoir 52, and lower reservoir valve 50 opens when pressure within lower reservoir 48 exceeds pressure within nozzle reservoir 52 by a pre-set amount. Thus as piston 30 descends, upper reservoir valve 46 opens, piston valve 36 closes, lower reservoir valve 50 opens, and medication 68 within lower reservoir 48 is forced out through lower reservoir valve 50, nozzle reservoir 52, stem bore 56 and nozzle outlet 62 as indicated by arrow 72.

After a dose of medication 68 has been administered, thumb rest 26 is released, and spring 34 urges piston assembly upwards until piston 30 butts against stop 27. As piston 30 ascends, upper reservoir valve 46 and lower reservoir valve 50 return to their closed position. At the same time, piston valve 36 returns to its normally open position, thus permitting lower reservoir 48 to fill with medication as indicated by arrow 67, thus making dispenser 20 ready to administer the next dose.

Method Used To Apply Topical Medication

One example of topical medication application using the instant method and apparatus is the case of hair growth drugs. Where the instant method and apparatus is used to apply hair growth medication to the scalp, a white horn hair having a diameter of 2–3 times normal hair diameter will be observed emerging from each pore. This horn hair will grow to a length of approximately two inches, and will crumble if cut and pressure is applied to it. After the drug-induced growth of normal hair has commenced, the horn hair will disappear.

When drug-induced growth of normal hair commences, the hair will initially be downy and white. After a period of time, the hair will assume the natural coloration of the subject taking the medication.

The instant method comprises the following steps:

A. Locating the pores in the area to which topical medication is to be administered;

B. Massaging the skin around each pore until each pore is open;

C. Installing a nozzle 58 having the correct size nozzle outlet 62;

D. Setting the position of nut 32 along rod 28 to provide the proper dose; and E. Applying medication using dispenser 20 as described above.

While a preferred embodiment of the invention has been illustrated herein, it is to be understood that changes and variations may be made by those skilled in the art without departing from the spirit of the appending claims.

DRAWING ITEM INDEX 2 skin
4 epidermis
6 dermis
8 connective fibrous tissue
10 sweat gland
12 pore
14 arteriole
16 venule 18 hair
19 thistle
20 dispenser
22 housing
23 housing bore
24 piston assembly
25 housing top
26 thumb rest
27 stop
28 rod
30 piston
31 rod thread
32 nut
34 spring
36 piston valve
38 cap
39 cap aperture
40 rod aperture
42 finger rest
44 upper reservoir
46 upper reservoir valve
48 lower reservoir
49 lower reservoir floor
50 lower reservoir valve
52 nozzle reservoir
54 stem
56 stem bore
58 nozzle
60 nozzle stem bore
62 nozzle outlet
64 arrow
66 arrow
67 arrow
68 medication
70 arrow
72 arrow

I claim:

1. A dispenser for applying topical medication comprising:
   a housing comprising a housing top having a normally closed upper reservoir valve and a rod aperture, a housing bore, a stop within said housing bore, and a lower reservoir floor having a normally closed lower reservoir valve; and
   a piston assembly comprising a rod slidably disposed within said rod aperture, a piston attached to one end of said rod, and a normally open piston valve disposed on said piston, said piston being sized to reciprocate within said housing bore between said stop and said lower reservoir floor.

2. The dispenser for applying topical medication of claim 1 wherein:
   said housing top, housing bore and piston define an upper reservoir, and said normally closed upper reservoir valve is designed to open when pressure exterior to said dispenser exceeds pressure within said upper reservoir; and
   said piston, housing bore and lower reservoir floor define a lower reservoir, and said normally open piston valve is designed to close when pressure within said lower reservoir exceeds pressure within said upper reservoir by a pre-set amount.

3. The dispenser for applying topical solution of claim 2 wherein said piston assembly further comprises a thumb rest attached to an extreme of said piston opposite said piston, a rod thread on said rod adjacent said thumb rest, a nut engaged with said rod thread, and a spring trapped in compression between said nut and said housing top whereby said piston is urged against said stop.

4. The dispenser of claim 3 wherein said dispenser further comprises a nozzle reservoir communicating with said lower reservoir through said normally closed lower reservoir valve, said normally closed lower reservoir valve being designed to open when pressure within said lower reservoir exceeds pressure within said nozzle reservoir by a pre-set amount.

5. The dispenser of claim 4 wherein said dispenser further comprises a nozzle, and said housing further comprises a stem having a stem bore, said stem bore communicating with said nozzle reservoir, said nozzle having a nozzle stem bore communicating with a nozzle outlet, said nozzle stem bore being sized to frictionally admit said nozzle stem, whereby said nozzle may be quickly and easily removed from said stem and replaced with a nozzle having a different nozzle outlet size.

6. The dispenser of claim 5 further comprising finger rests rigidly attached to said housing, a cap aperture in said housing top whereby said dispenser may be conveniently filled with topical medication, and a cap sized to fit into said cap aperture.

7. A method of applying topical medication using a dispenser, said dispenser comprising:
   a housing comprising a housing top having a normally closed upper reservoir valve, rod aperture and cap aperture, a housing bore, a stop within said housing bore, and a lower reservoir floor having a normally closed lower reservoir valve, a lower reservoir communicating with an exterior of said dispenser through said lower reservoir valve and a removable nozzle; and
   a piston assembly comprising a rod slidably disposed within said rod aperture, a piston attached to one end of said rod, and a normally open piston valve disposed on said piston, said piston being sized to reciprocate within said housing bore between said stop and said housing floor;
   said method comprising the steps of:
   A. Locating pores in an area to which topical medication is to be administered;
   B. Massaging skin around each said pore until each said pore is open; and
   C. Applying medication to each said pore using said dispenser.

8. The method of claim 7 further comprising the step of installing one said nozzle having a nozzle outlet of proper size for medication to be applied and body area to which the medication is to be applied.

9. The method of claim 7 wherein said piston assembly further comprises a thumb rest attached to an extreme of said piston opposite said piston, a rod thread on said rod adjacent said thumb rest, a nut engaged with said rod thread, and a spring trapped in compression between said nut and said housing top whereby said piston is urged against said stop, and whereby rotation of said nut relative to said rod determines an amount of medication dispensed during each piston stroke, and wherein said method comprises the further step of setting an amount of medication to be dispensed by rotating said nut about said rod on said rod thread.

* * * * *